United States Patent
Brady et al.

(10) Patent No.: US 9,463,036 B2
(45) Date of Patent: Oct. 11, 2016

(54) CLOT ENGAGEMENT AND REMOVAL SYSTEM

(75) Inventors: Eamon Brady, Loughrea (IE); Michael Gilvarry, Headford (IE); Mahmood K. Razavi, Irvine, CA (US); David Vale, Barna (IE)

(73) Assignee: Neuravi Limited, Galway (IE)

( * ) Notice: Subject to any disclaimer, the term of this patent is extended or adjusted under 35 U.S.C. 154(b) by 258 days.

(21) Appl. No.: 13/823,048

(22) PCT Filed: Oct. 21, 2011

(86) PCT No.: PCT/IE2011/000057
§ 371 (c)(1),
(2), (4) Date: Mar. 13, 2013

(87) PCT Pub. No.: WO2012/052982
PCT Pub. Date: Apr. 26, 2012

(65) Prior Publication Data
US 2013/0197567 A1     Aug. 1, 2013

Related U.S. Application Data

(60) Provisional application No. 61/344,848, filed on Oct. 22, 2010.

(51) Int. Cl.
*A61M 29/00* (2006.01)
*A61B 17/221* (2006.01)
*A61B 17/22* (2006.01)

(52) U.S. Cl.
CPC ...... *A61B 17/221* (2013.01); *A61B 2017/2212* (2013.01); *A61B 2017/2217* (2013.01); *A61B 2017/22034* (2013.01); *A61B 2017/22094* (2013.01)

(58) Field of Classification Search
CPC .................. A61B 17/221; A61B 2017/2212; A61B 2017/22034
See application file for complete search history.

(56) References Cited

U.S. PATENT DOCUMENTS 4,793,348 A     12/1988 Palmaz
4,873,978 A     10/1989 Ginsburg
(Continued)

FOREIGN PATENT DOCUMENTS

DE     202009001951 U1    4/2010
DE     102009056450 A1    6/2011
(Continued)

OTHER PUBLICATIONS

US 6,348,062, 02/2002, Hopkins et al. (withdrawn)
(Continued)

*Primary Examiner* — Gregory Anderson
*Assistant Examiner* — Son Dang
(74) *Attorney, Agent, or Firm* — Bookoff McAndrews, PLLC

(57) ABSTRACT

A clot retrieval apparatus 1 comprises a clot engaging device 2 and a capture basket 3. The clot engaging device 2 has a collapsed delivery configuration and an expanded deployment configuration. The clot engaging device has a proximal end and a distal end and an elongate body between the proximal end and the distal end. The capture basket 3 has a collapsed delivery configuration and an expanded deployment configuration. The capture basket 3 has a proximal mouth which is open when the capture basket 3 is in the deployment configuration. The clot engaging device 2 is axially movable relative to the capture basket for capture of a clot.

20 Claims, 5 Drawing Sheets

(56) References Cited

U.S. PATENT DOCUMENTS

| | | |
|---|---|---|
| 5,011,488 A | 4/1991 | Ginsburg |
| 5,092,839 A | 3/1992 | Kipperman |
| 5,122,136 A | 6/1992 | Guglielmi et al. |
| 5,171,233 A | 12/1992 | Amplatz |
| 5,234,437 A | 8/1993 | Sepetka |
| 5,387,219 A | 2/1995 | Rappe |
| 5,387,226 A | 2/1995 | Miraki |
| 5,449,372 A | 9/1995 | Schmaltz |
| 5,538,512 A | 7/1996 | Zenzon et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,695,519 A | 12/1997 | Summer et al. |
| 5,709,704 A | 1/1998 | Nott et al. |
| 5,713,853 A | 2/1998 | Clark |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Daniel et al. |
| 5,827,304 A | 10/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,947,995 A | 9/1999 | Samuels |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,179,861 B1 | 1/2001 | Khosravi |
| 6,203,561 B1 * | 3/2001 | Ramee et al. ............... 606/200 |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,312,444 B1 | 11/2001 | Barbut |
| 6,325,819 B1 | 12/2001 | Pavcnik et al. |
| 6,336,934 B1 | 1/2002 | Gilson et al. |
| 6,348,056 B1 | 2/2002 | Bates |
| 6,350,271 B1 | 2/2002 | Kurz et al. |
| 6,361,545 B1 | 3/2002 | Macoviak |
| 6,383,205 B1 | 5/2002 | Samson et al. |
| 6,383,206 B1 | 5/2002 | Gillick |
| 6,402,771 B1 | 6/2002 | Palmer |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,994,718 B2 | 2/2006 | Groothuis et al. |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,175,655 B1 | 2/2007 | Malaei |
| 7,179,273 B1 | 2/2007 | Palmer et al. |
| 7,220,271 B2 | 5/2007 | Clubb |
| 7,229,472 B2 | 6/2007 | DePalma et al. |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Clubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin, Jr. et al. |
| 7,618,434 B2 | 11/2009 | Santra |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |

(56) References Cited

U.S. PATENT DOCUMENTS

| | | |
|---|---|---|
| 7,828,815 B2 | 11/2010 | Mazzocchi |
| 7,846,175 B2 | 12/2010 | Bonnette et al. |
| 7,846,176 B2 | 12/2010 | Gilson et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,361,095 B2 | 1/2013 | Osborne |
| 8,366,663 B2 | 2/2013 | Fiorella et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,814,925 B2 | 8/2014 | Hilaire et al. |
| 8,900,265 B1 | 12/2014 | Ulm, III |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 2001/0001315 A1 | 5/2001 | Bates |
| 2001/0016755 A1 | 8/2001 | Addis |
| 2001/0051810 A1 | 12/2001 | Dubrul |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barbut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0040772 A1 | 2/2003 | Hyodoh et al. |
| 2003/0050663 A1 | 3/2003 | Khachin |
| 2003/0125798 A1 | 7/2003 | Martin |
| 2003/0144687 A1 | 7/2003 | Brady et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0176884 A1 | 9/2003 | Berrada et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0236533 A1 | 12/2003 | Wilson |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung et al. |
| 2004/0153118 A1 | 8/2004 | Clubb |
| 2005/0033348 A1 | 2/2005 | Sepetka |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0125024 A1 | 6/2005 | Sepetka |
| 2005/0171566 A1 | 8/2005 | Kanamaru |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0267491 A1* | 12/2005 | Kellett et al. ............ 606/113 |
| 2005/0288686 A1 | 12/2005 | Sepetka |
| 2006/0009799 A1 | 1/2006 | Kleshinski et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0155305 A1 | 7/2006 | Freudenthal |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0156170 A1 | 7/2007 | Hancock |

(56) References Cited

U.S. PATENT DOCUMENTS

| | | |
|---|---|---|
| 2007/0165170 A1 | 7/2007 | Fukuda |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0225749 A1 | 9/2007 | Martin |
| 2007/0244505 A1 | 10/2007 | Gilson et al. |
| 2007/0270902 A1 | 11/2007 | Slazas et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1* | 10/2008 | Jenson ............... A61B 17/221 606/159 |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0312681 A1 | 12/2008 | Ansel |
| 2009/0024157 A1 | 1/2009 | Anukhin |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0292297 A1 | 11/2009 | Ferrere |
| 2009/0292307 A1 | 11/2009 | Razack |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1* | 10/2010 | Bonnette et al. ............ 606/200 |
| 2010/0268265 A1 | 10/2010 | Krolik et al. |
| 2010/0318178 A1 | 12/2010 | Rapaport et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0022149 A1 | 1/2011 | Cox et al. |
| 2011/0054504 A1 | 3/2011 | Porter |
| 2011/0054514 A1 | 3/2011 | Arcand |
| 2011/0054516 A1 | 3/2011 | Keegan |
| 2011/0060359 A1 | 3/2011 | Hannes |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213403 A1 | 9/2011 | Aboytes |
| 2011/0224707 A1 | 9/2011 | Miloslavski et al. |
| 2011/0276120 A1 | 11/2011 | Gilson et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0089216 A1 | 4/2012 | Rapaport et al. |
| 2012/0143237 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0277788 A1 | 11/2012 | Cattaneo |
| 2012/0296362 A1 | 11/2012 | Cam et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0180377 A1 | 6/2014 | Bose et al. |
| 2014/0194919 A1 | 7/2014 | Losordo et al. |
| 2014/0200608 A1 | 7/2014 | Brady et al. |
| 2014/0236220 A1 | 8/2014 | Inoue |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0112376 A1 | 4/2015 | Molaei et al. |
| 2015/0133990 A1 | 5/2015 | Davidson |
| 2015/0164523 A1 | 6/2015 | Brady et al. |
| 2015/0250497 A1 | 9/2015 | Marks et al. |
| 2015/0257775 A1 | 9/2015 | Gilvarry et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Seifert et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |

FOREIGN PATENT DOCUMENTS

| | | |
|---|---|---|
| DE | 102010010849 A1 | 9/2011 |
| DE | 10 2010 014778 A1 | 10/2011 |
| DE | 102010024085 A1 | 12/2011 |
| DE | 102011014586 B3 | 9/2012 |
| EP | 2301450 B1 | 11/2011 |
| EP | 2628455 A1 | 2/2013 |
| JP | 0919438 A | 1/1997 |

(56) References Cited

FOREIGN PATENT DOCUMENTS

| | | |
|---|---|---|
| WO | WO 94/24926 | 11/1994 |
| WO | WO 97/27808 | 8/1997 |
| WO | WO 97/38631 A1 | 10/1997 |
| WO | WO 99/20335 | 4/1999 |
| WO | WO 99/60933 | 12/1999 |
| WO | WO 99/56801 | 4/2000 |
| WO | WO 01/21077 | 3/2001 |
| WO | WO 02/02162 | 1/2002 |
| WO | WO 02/11627 | 2/2002 |
| WO | WO 02/43616 | 6/2002 |
| WO | WO 02/070061 | 9/2002 |
| WO | WO 02/094111 | 11/2002 |
| WO | WO 03/002006 | 1/2003 |
| WO | WO 03/030751 | 4/2003 |
| WO | WO 03/051448 | 6/2003 |
| WO | WO 2004/028571 A2 | 4/2004 |
| WO | WO 2004/056275 A1 | 7/2004 |
| WO | WO 2005/000130 A1 | 1/2005 |
| WO | WO 2005/027779 A2 | 3/2005 |
| WO | WO 2006/021407 | 3/2006 |
| WO | WO 2006/031410 | 3/2006 |
| WO | WO 2006/107641 | 10/2006 |
| WO | WO 2006/135823 A2 | 12/2006 |
| WO | WO 2007/054307 | 5/2007 |
| WO | WO 2007/068424 | 6/2007 |
| WO | WO 2008/034615 | 3/2008 |
| WO | WO 2008/051431 A1 | 5/2008 |
| WO | WO 2008/131116 | 10/2008 |
| WO | WO 2009/031338 A1 | 3/2009 |
| WO | WO 2009/076482 | 6/2009 |
| WO | WO 2009/076482 A1 | 6/2009 |
| WO | WO 2009/086482 A1 | 7/2009 |
| WO | WO 2009/105710 A1 | 8/2009 |
| WO | WO 2010/010545 A1 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/066961 A1 | 6/2011 |
| WO | WO 2011/082319 A1 | 7/2011 |
| WO | WO 2011/095352 A1 | 8/2011 |
| WO | WO 2011/110316 A1 | 9/2011 |
| WO | WO 2011/135556 A1 | 11/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/120490 A2 | 9/2012 |
| WO | WO 2012/110619 A9 | 10/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/134625 A1 | 9/2015 |
| WO | WO 2015/179324 A2 | 11/2015 |
| WO | WO 2016/010995 A1 | 1/2016 |

OTHER PUBLICATIONS

International Search Report of PCT/IE2011/000057 dated Feb. 3, 2012.
International Search Report of PCT/IE2012/000011, dated Oct. 10, 2012, 3 pages.
Written Opinion and International Search Report, dated Jul. 27, 2011, from international Application No. PCT/IE2011/000026, 7 pages.

\* cited by examiner

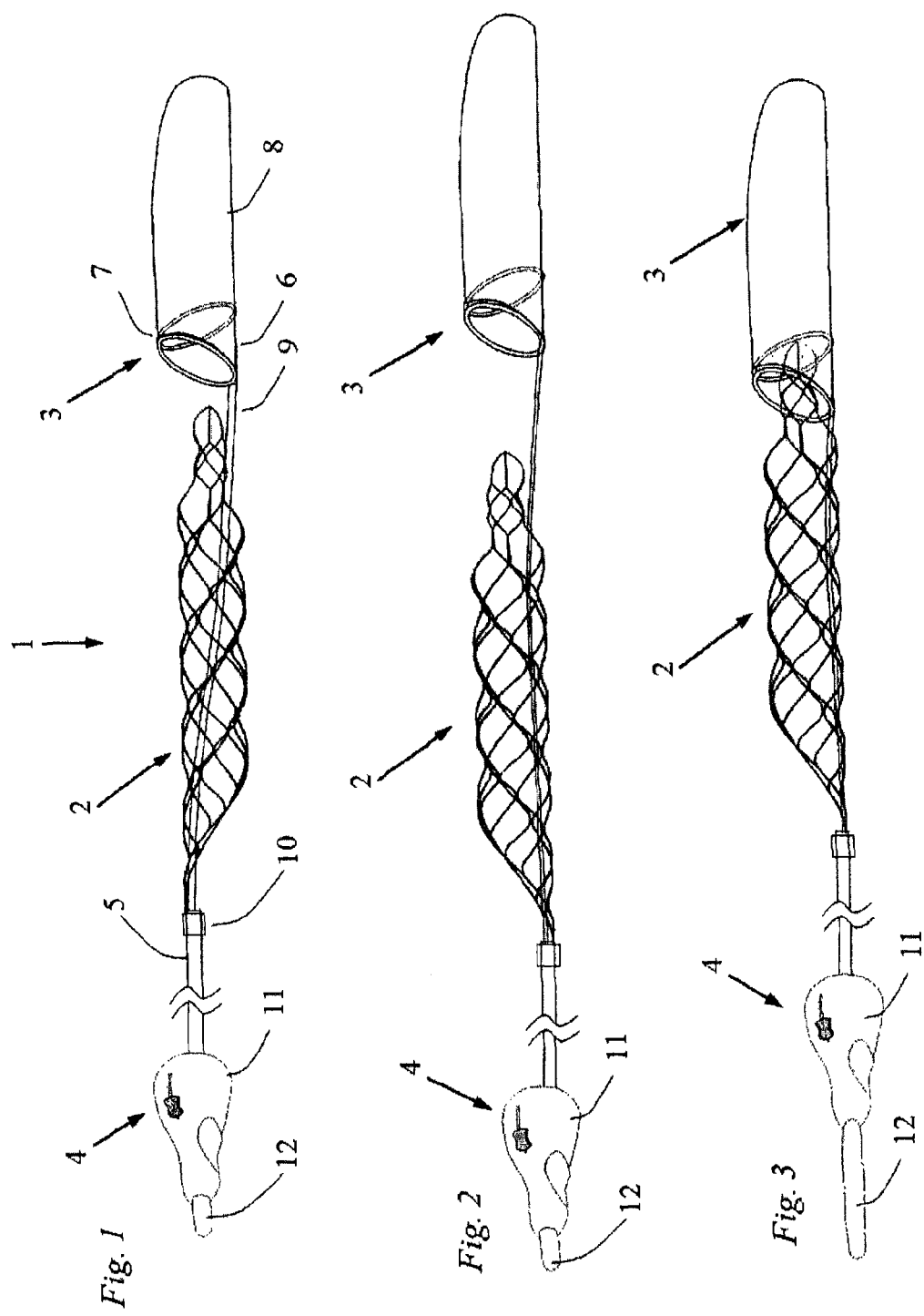

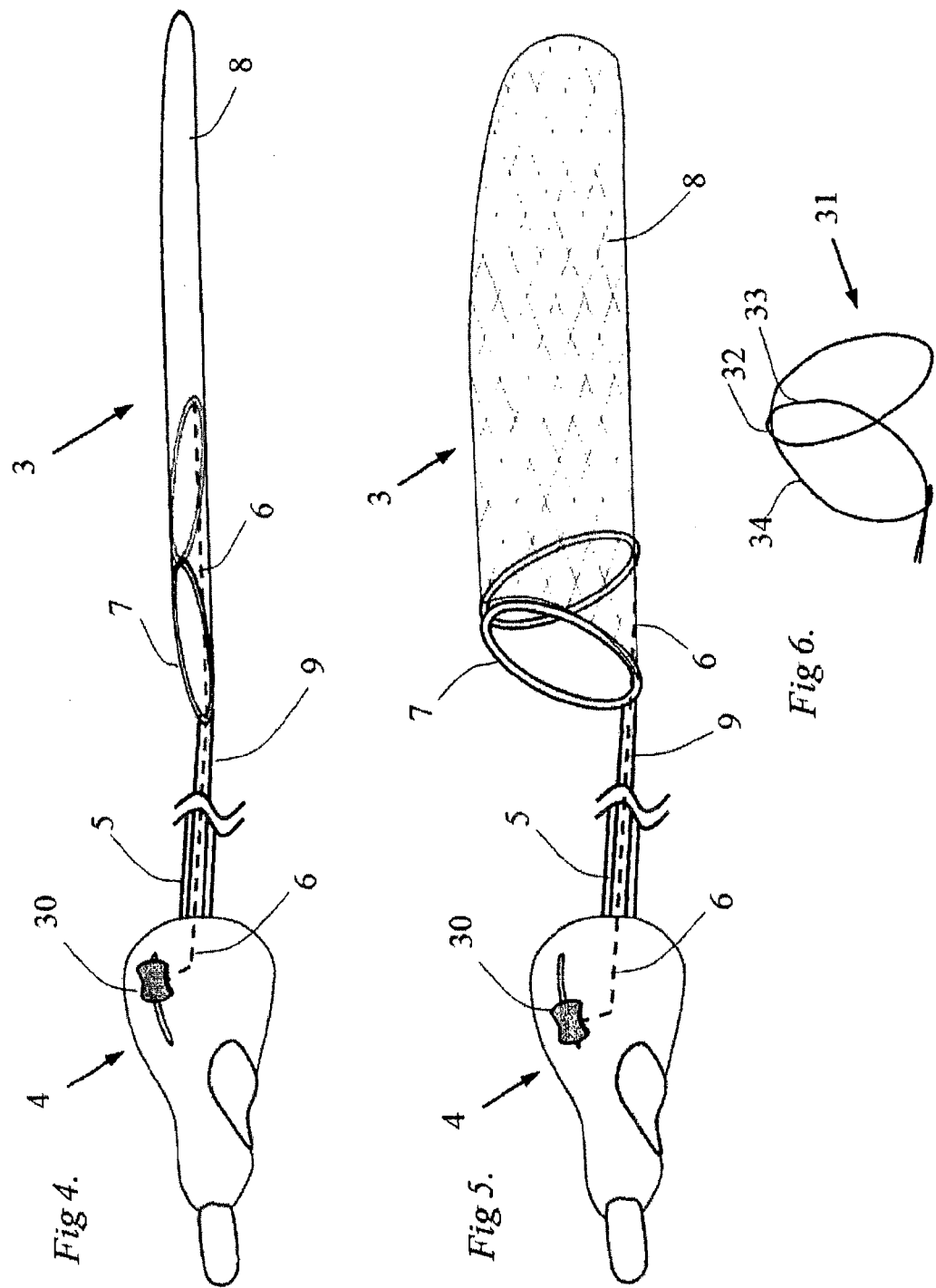

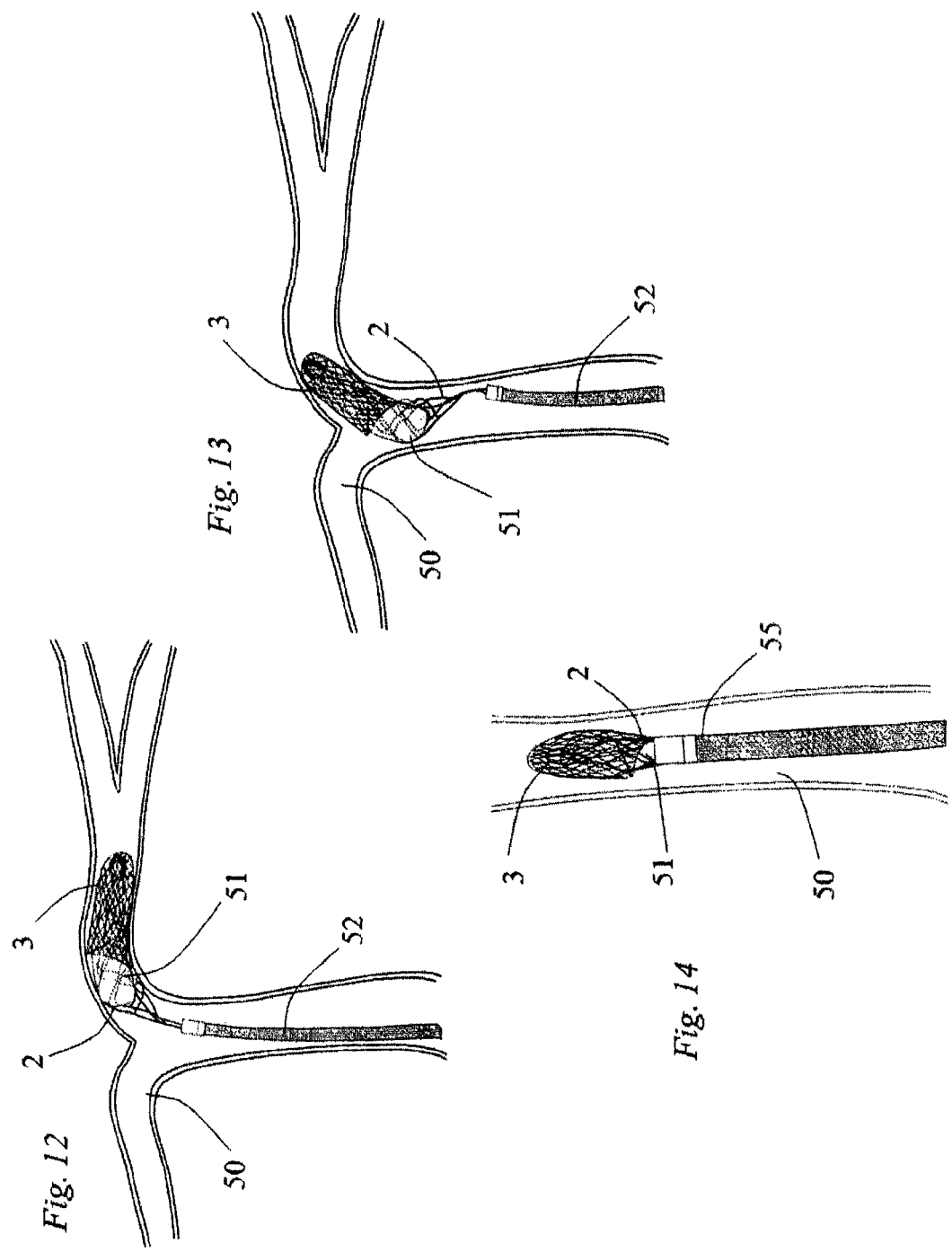

CLOT ENGAGEMENT AND REMOVAL SYSTEM

CROSS REFERENCE TO RELATED APPLICATION

This application is a National Stage of International Application No. PCT/IE2011/000057 filed Oct. 21, 2011, which claims priority from U.S. Provisional Application No. 61/344,848 filed Oct. 22, 2010, the contents of all of which are incorporated herein by reference in their entirety.

The invention relates to devices, and methods of removing acute blockages from blood vessels. The invention especially relates to removing acute obstructions from blood vessels. Acute obstructions may include clot, misplaced devices, migrated devices, large emboli and the like. More particularly the invention relates to removing clot from cerebral arteries in patients suffering acute ischemic stroke.

Accessing the neurovascular bed is difficult with conventional technology as the target vessels are small in diameter, are remote relative to the site of insertion and are highly tortuous. Despite the fact that there are over 600,000 acute ischemic strokes in the US each year, clot retrieval devices are used to treat patients in less than <1% of cases. The reasons for this are that conventional technology is either too large in profile, lacks the deliverability to navigate tortuous vessels or is not effective at removing clot when delivered to the target site.

There are significant challenges associated with designing clot removal devices that can deliver high levels of performance. Firstly, there are a number of access challenges that make it difficult to deliver devices. In some patients the configuration of the aortic arch makes it difficult to position a guide catheter in the larger arteries that supply blood to the brain. These difficult arch configurations are classified as either type 2 or type 3 aortic arches with type 3 arches presenting the most difficulty. The tortuousity challenge is even more severe in the arteries approaching the brain. It is not unusual at the distal end of the internal carotid artery that the device will have to navigate a vessel segment with a 180° bend, a 90° bend and a 360° bend in quick succession over a few centimeters of vessel.

Secondly, neurovascular vessels are more fragile than similarly sized vessels in other parts of the body and are in a soft tissue bed. This issue is compounded by the fact that in many instances the clot is firmly wedged in the vessel. More mature and organized clot material is likely to be less compressible than softer fresher clot, and under the action of blood pressure it may distend the compliant vessel in which it is lodged. Thirdly, the clot may comprise any of a range of morphologies and consistencies. In particular long strands of softer clot material may tend to lodge at bifurcations or trifurcations in cerebral vessels, resulting in multiple vessels being simultaneously occluded.

Self expanding stent-like devices referred to as "stentrievers" are sometimes used to remove clot from cerebral vessels of acute stroke patients. These devices generally pin the clot between the device and vessel wall and embed somewhat into the clot so that the clot can be withdrawn with the device. One disadvantage with this approach is that it relies on pinning the clot between the stentriever and the vessel wall and thus may not restrain the clot effectively when passing a branch vessel or when passing into a vessel that is larger than the fully expanded diameter of the stentriever. Another disadvantage of stentrievers is that they use their radial force to embed in and grip the clot. With soft clot a low level of radial force may be effective, but with firmer clot the level of radial force required to effectively grip the clot may be higher than that which can be safely applied to a cerebral vessel. Therefore stentrievers that have sufficient radial force to deal with all clot types may cause vessel trauma and serious patient injury, and stentrievers that have appropriate radial force to remain atraumatic may not be able to effectively handle all clot types.

The present invention is directed towards providing devices and methods which will address at least some of these issues.

STATEMENTS OF INVENTION

The invention provides a clot retrieval apparatus which comprises a clot engaging device and a capture basket. The clot engaging device has a collapsed delivery configuration and an expanded deployment configuration, the clot engaging device also has a proximal end and a distal end and an elongate body between the proximal end and the distal end. The capture basket has a collapsed delivery configuration and an expanded deployment configuration, the capture basket also has a proximal mouth which is open when the capture basket is in the deployed configuration. The clot engaging device is axially movable for capture of a clot In one aspect the invention provides a clot retrieval apparatus comprising:
  a clot engaging device and a capture basket;
  the clot engaging device having a collapsed delivery configuration and an expanded deployment configuration, the clot engaging device having a proximal end and a distal end and an elongate body between the proximal end and the distal end, the clot engaging device being connected to a first elongate shaft element;
  the capture basket having a collapsed delivery configuration and an expanded deployment configuration, the capture basket having a proximal mouth which is open when the capture basket is in the deployed configuration, the capture basket being connected to a second elongate shaft element, and
  the shaft elements being movable relative to one another such that the clot engaging device is axially movable relative to the capture basket for capture of a clot.

In another aspect the invention provides an apparatus for retrieving clot from a blood vessel of a patient comprising:
  an elongate shaft, a clot engaging device and a capture basket;
  the elongate shaft comprising at least two elongate elements and comprising a distal section and a proximal section, the proximal section extending exterior of the patient, and;
  the clot engaging device comprising a plurality of struts defining a structure having a collapsed delivery configuration and an expanded deployment configuration, and having a proximal end and a distal end, and being attached at its proximal end to the distal section of a first elongate element of the shaft;
  the capture basket comprising a structure with a capture net and an inlet mouth and having a collapsed delivery configuration and an expanded deployment configuration, and being attached at its proximal end to the distal section of a second elongate element of the shaft;
  the capture basket being axially movable relative to the clot engaging device to pin a clot between the two structures.

In one embodiment at least the distal end of the clot engaging device is movable to enter the proximal mouth of the capture basket for capture of a clot.

In one case the elongate body of the clot engaging device comprises a distal section, a proximal section and an intermediate section between the proximal and the distal sections.

In one embodiment in the deployed configuration, the distal section of the clot engaging device has a diameter which is smaller than a diameter of the intermediate section.

In one case in the deployed configuration, the proximal section of the clot engaging device has a diameter which is smaller that a diameter of the intermediate section.

In the deployed configuration, at least the intermediate section of the clot engaging device may have a generally tubular shape.

In one embodiment the clot engaging device comprises a mesh.

The mesh may comprise a plurality of struts. At least some of the struts may form closed cells.

In one embodiment the clot engaging device defines a pathway for the second shaft element.

In one case the capture basket comprises a capture net and a support frame for the capture net.

The support frame may be connected to the second shaft element.

In one embodiment the clot retrieval apparatus comprises a control element which extends proximally from the support frame of the capture basket for operation by a user. The control element may comprise a tether for controlling the operation of the frame.

The invention also provides various methods for retrieving clot from a blood vessel of a patient.

In one aspect the clot retrieval method comprises the steps of
providing a clot retrieval apparatus comprising an engaging device and a capture basket;
crossing a clot with a microcatheter;
advancing the clot retrieval apparatus through the microcatheter and across the clot;
deploying the capture basket distal of the clot;
deploying the clot engaging device within the clot at an initial deployment site;
retracting the clot engaging device and the capture basket together to a location proximal of the initial deployment site;
retracting the capture basket towards the clot engaging device to capture the clot therebetween; and
withdrawing the clot engaging device, the capture basket and the captured clot proximally.

BRIEF DESCRIPTION OF THE DRAWINGS

The invention will be more clearly understood from the following description of some embodiments thereof, given by way of example only, with reference to the accompanying drawings, in which:

FIG. 1 is a side view of a device according to the invention for removing an obstruction to a vessel;

FIG. 2 is a side view of a similar device for removing an obstruction to a vessel;

FIG. 3 illustrates the device of FIG. 2 with a distal basket retracted relative to a clot engaging section;

FIGS. 4 and 5 are side views of the basket of the device in the collapsed and expanded configurations respectively;

FIG. 6 is a side view of a frame in a figure of eight pattern;

FIGS. 8 to 14 illustrate one method of use of a device of the invention.

DETAILED DESCRIPTION

Figure 7:
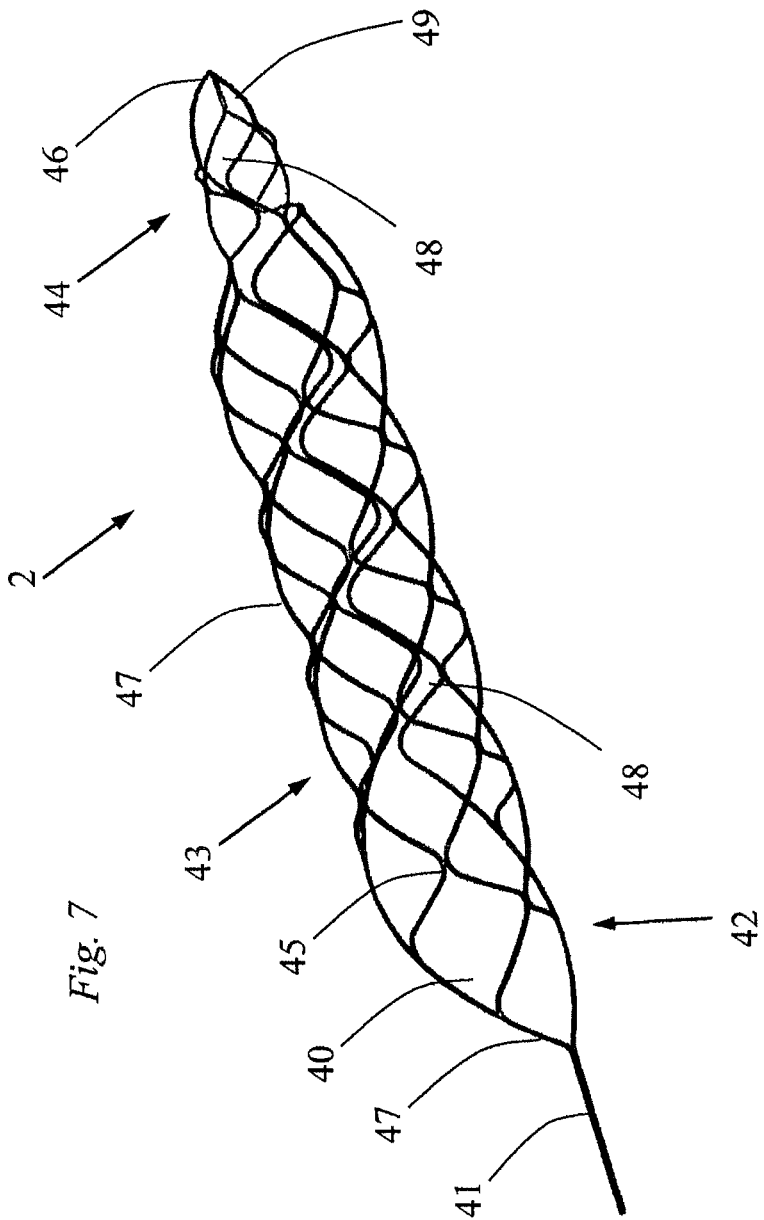
FIG. 7 is an isometric view of a clot engaging portion of a device of the invention.

The invention provides an apparatus and methods for the removal of obstructions in vessels. In particular, the invention is directed towards the treatment of occlusions to blood vessels, especially arterial vessels, and more particularly the removal of occlusive clots from cerebral arterial vessels.

With reference to FIG. 1 there is shown a schematic representation of a device 1 according to the invention for the removal of an obstruction to a vessel. The device 1 comprises a clot engaging device 2 and a capture basket 3. The clot engager 2 has a collapsed state for delivery through the vasculature and an expanded state for engagement with the clot and for disengaging the clot from the vessel wall. The clot engager 2 is connected to a first elongate shaft element which in this case is provided by a support shaft 5 by means of collar 10 or by any other suitable joining method. The support shaft 5 may be connected at its proximal end to a first element 11 of a handle 4. The capture basket 3 has a collapsed configuration for delivery and an expanded configuration for clot engagement and capture. The capture basket 3 comprises a frame 7 and a capture net 8. The frame 7 is connected to a second elongate shaft element which in this case is provided by a support shaft 9. The shaft 9 may be connected at its proximal end to a second element 12 of the handle 4.

The device is configured so that relative movement may be effected between the clot engager 2 and the capture basket 3. In the embodiment shown this movement may be effected by relative movement of components 11 and 12 of the handle 4 which are connected to the shaft elements 5, 9. In another embodiment the handle 4 is detachable from the shaft and in yet another embodiment the device is configured without any handle.

In one embodiment the device is configured so that at least a distal portion of the clot engager 2 can enter the capture basket 3. The degree to which the clot engager can enter the basket 3 may be controlled by limiting the travel of the shaft 9 relative to the shaft 5. The limiter may be provided for example by a stop on the shaft 9 as the clot engager 2 is connected to the shaft 5 and the basket is connected to the shaft 9.

In one case the clot engager 2 comprises multiple struts. The struts may form at least one closed cell. The shaft 9 may pass through at least one of the closed cells. In another embodiment the clot engager 2 comprises multiple struts, forming multiple cells and forming a generally tubular shape, with at least one open seam along the length of the engager 2, and with the shaft 9 passing through one of said seams. In one embodiment the shaft 9 is positioned partially within and partially outside of the clot engager 2 in the expanded configuration and fully within the clot engager in the wrapped configuration, passing from within to without via a pathway defined by a seam extending to the distal end of the device.

FIG. 2 illustrates a device similar to FIG. 1 in which like parts were assigned the same reference numerals. In this case the clot engager 2 is positioned proximal of the capture basket 3. FIG. 3 shows the device of FIG. 2 in a configuration in which the capture basket 3 has been retracted over the distal end of the clot engager 2 by movement of the second handle element 12 relative to the first handle element 11.

FIGS. 4 and 5 are side views of the proximal and distal ends of a device of the invention in which a clot engager portion is omitted. In the embodiment illustrated the capture basket 3 has a control tether 6 that can be tensioned to control the expansion of the frame 7 of the clot basket 3 or to increase the radial force of the frame 7 of the clot basket 3. The user can control the diameter to which the frame 7 expands by controlling the position of a movable control element such as a button 30 on the handle 4. FIG. 4 shows the control button 30 in an advanced position with the basket 3 in a collapsed configuration. This collapsed configuration of the device facilitates loading and advancement through a microcatheter. In this configuration the frame 7 has a low expansion force and is thus very flexible and easy to deliver.

FIG. 5 shows the frame 7 in an expanded configuration. In this configuration the control button 30 is in a retracted position to tension and withdraw the tether 6 and thus expand and strengthen the frame 7. In one embodiment the frame 7 and the basket 3 can be set to different diameters by adjusting the position of the button 30.

FIG. 6 illustrates one embodiment of a frame 31 in which the frame 31 is formed in a figure of eight pattern so that frame struts 33 and 34 at crossover point 32 can move relative to each other to facilitate the adjustment of the frame to different vessel diameters.

FIG. 7 is an isometric view of a clot engagement device 2 of the invention. The clot engagement device 2 has a proximal end 41 and a distal end 46, and between these ends there are a proximal section 42, a mid section 43 and a distal section 44. Multiple struts 47 connect one end of the device to the other. In certain sections of the device the struts 47 are configured to form cells 40 with connecting apices 45. In one case (as shown in FIG. 7) the distal section 44 has a smaller diameter than the mid section 43, so that the distal section may enter the mouth of a basket or capture net (not shown). In one case (as shown in FIG. 7) the cells 40 are not fully connected around the device circumference at all points along the length of the device, effectively leaving an open seam 48 extending from the proximal end to distal end. This seam provides a pathway through which an elongate shaft entering the device through the open mouth of section 40 may exit the middle section 43 or distal section 44 of the device, such as shown in FIGS. 1, 2 and 3. Thus the distal end of device 2 may enter the mouth of a basket attached to the end of such a shaft, such as illustrated in FIG. 3 by way of example. In another embodiment the seam may run only partially along the length of the device, spanning at least the distal section 44 where it provides an exit pathway for the elongate shaft. This seam may run axially along the device as shown or may run in a more helical-like pattern around the device, or may be staggered and discontinuous, said seam patterns providing additional engagement features to aid in gripping of the target clot. The distal end 46 is in this case configured to enter capture basket 3 of the device of FIG. 1. Distal struts 49 act as guide rails in the embodiment shown to facilitate this entry by providing a smooth and snag free surface to contact and pass through the inlet mouth 34 of the frame 31 in FIG. 6 of a capture basket The material of the device may be nitinol or another superelastic or shape memory material, and may be formed from multiple wires or may be cut from a tube or a flat sheet, and may be heat set to define a preferred expanded geometry.

FIGS. 8 to 14 show a series of procedural steps associated with using the device 1. The standard steps involved to place a guide or sheath access catheter and cross the clot with a guidewire and microcatheter are not shown, but will be easily understood by one skilled in the art.

Figure 8:
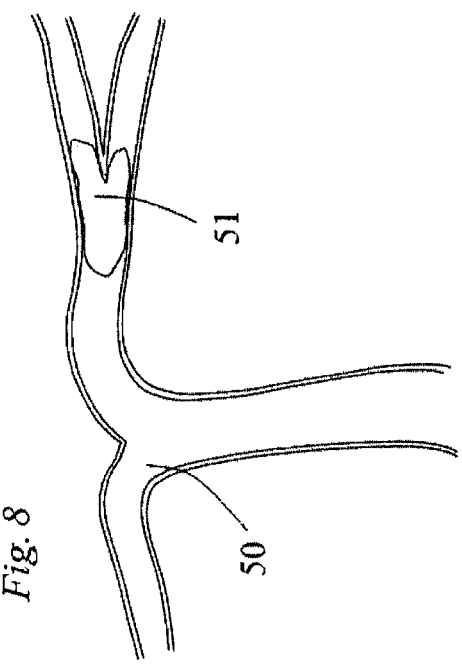

FIG. 8 shows a clot 51 lodged in a bifurcation with vasculature 50.

Figure 9:
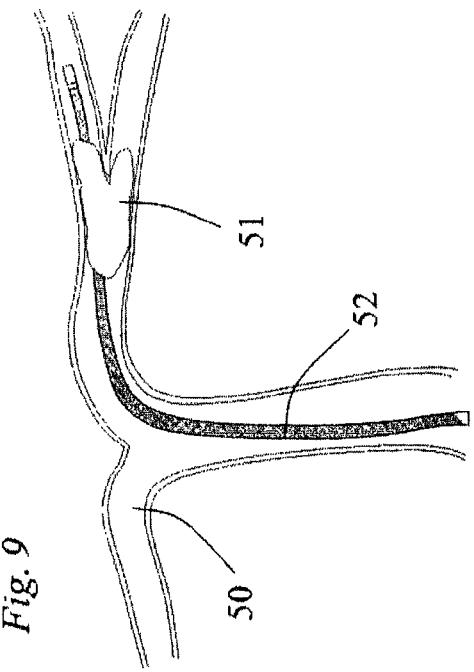

FIG. 9 shows a microcatheter 52 that has been advanced across the clot 51, typically with the aid of a guidewire (not shown) which is then withdrawn to leave the lumen of the microcatheter free for the advancement of a clot retrieval device.

Figure 10:
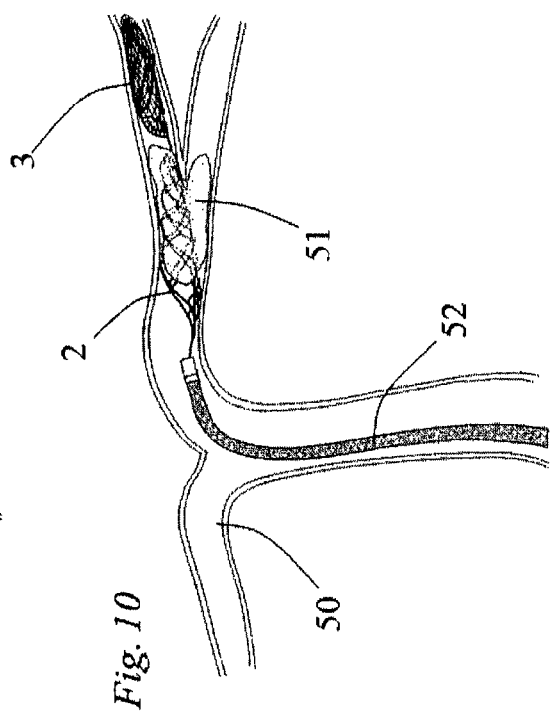

The clot retrieval device is then loaded into the proximal end of the microcatheter 52 and advanced to a target deployment site with the aid of fluoroscopy. The device is positioned so that the capture basket 3 is distal of the clot 51 and at least a portion of the engager 2 is within the clot. The microcatheter 52 is then retracted allowing the devices to deploy and expand as shown in FIG. 10. The clot engager 2 expands and engages with body of the clot 51. If the basket 3 employs a tether activation system as described above the tether may be tensioned to effect deployment of the basket 3 or to increase the opening force so that the basket can engage and encapsulate clot without collapse.

Figure 11:
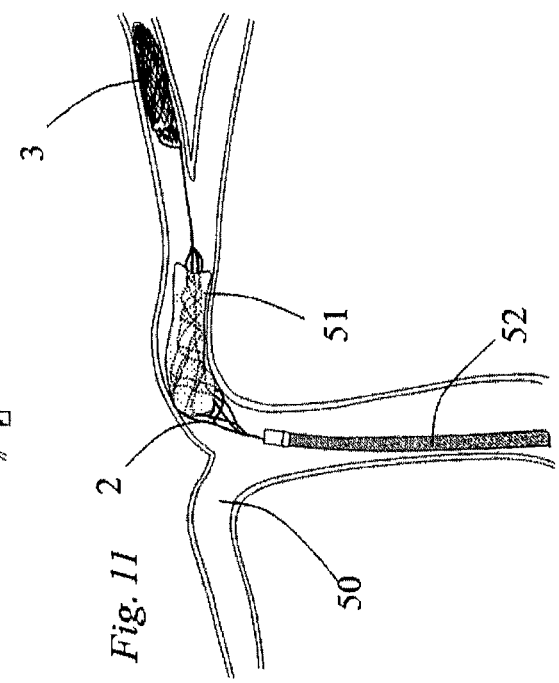

The clot engager 2 is then retracted, pulling the clot 51 out of the bifurcation and into a more proximal section of the vasculature as shown in FIG. 11.

The capture basket 3 can then be retracted to encapsulate some or all of the clot 51 and the 30 engager 2 and to pin the clot 51 between the engager 2 and the basket 3 as shown in FIG. 12.

The engager 2, basket 3 and captured clot 51 can then be safely withdrawn proximally with clot held securely as the system passes any branch vessels and into larger proximal vasculature as shown in FIG. 13.

FIG. 14 shows the device and clot being withdrawn into a guide catheter or sheath 55.

Removal of the device and captured clot may be assisted by the use of a distal access catheter or similar device with or without the use of aspiration. A flow obstructing cuff on the distal end of a guide catheter or sheath may also be employed to aid in the effectiveness of the use of aspiration while extracting the device and captured clot from the patient.

An alternative sequence of steps that may be used with the device of this invention would involve:
  crossing the clot with a microcatheter as described above;
  advancing the clot retrieval device through the microcatheter and across the clot;
  withdrawing the microcatheter to a location proximal of the clot to leave the capture basket deployed distal of the clot and the clot engager deployed within the clot;
  retracting the clot engager and capture basket together to a location proximal of the initial deployment site;
  retracting the capture basket a further distance towards and over the clot engager; and
  withdrawing the clot engager, the capture basket and the captured clot proximally out of the patient.

Another of the many ways in which a device of this invention may be employed involves the use of a variant of the device without a handle or with a detachable handle. Such a device may be deployed across the clot as described in one of the methods above, after which the basket may be left in place protecting the distal vessel bed while the clot engager is advanced and withdrawn multiple times to remove clot. This system has the advantage that the basket shaft acts a guide rail to facilitate rapid re-advancement of the clot engager to the target site on each pass. An extension wire may be added to the proximal end of the basket shaft 9 to enable the user to maintain good control of the basket while removing the clot engager from the patient between passes. Alternatively the clot engager 2 and its shaft 5 may be configured in the manner of a rapid exchange catheter so that they can be advanced and retracted over the basket shaft 9 without the need for any extension wire.

It will be understood from all of the above that this device has features that enable it to be used in a variety of different ways to retrieve obstructions from vessel, so that the precise method of use can be tailored to suit the specific needs of any given situation. The clot engager is designed to engage with clot by means of the engager struts, and more specifically the distal apices of the engager cells, embedding in and snagging the clot. Expansion of the engager also pins the clot between the engager and the vessel wall and assists this embedding process. The basket frame 7 is designed to engage the clot from its distal end and assists in guiding the capture net 8 over the clot. The frame 7 and engager 2 can also be used to pin the clot between these two elements of the device. This is of particular advantage in ensuring that a firm grip is held on the clot as it is withdrawn against the flow past branch vessels and into larger more proximal vasculature. The clot engager may also be employed to constrain the clot while the basket is withdrawn over the clot. This may be of particular advantage in cases where the clot is firmly lodged in the vessel and a significant force is required to disengage and remove it. Using the clot engager in a compressive mode while retracting the basket over the clot shields the distal vasculature from potentially traumatic tensile forces that would otherwise be exerted on them.

Accessing cerebral vessels involves the use of a number of commercially available products and conventional procedural steps. Access products such as guidewires, guide catheters and microcatheters are known and are regularly used in procedures carried out in cerebral vessels. Such systems are described for example in WO2010/010545A and U.S.20110160763A the entire contents of which are incorporated herein by reference.

Modifications and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiments hereinbefore described which may be varied in construction and detail.

The invention claimed is:

1. A clot retrieval apparatus, comprising:
   a handle;
   a clot engaging device located distally of the handle and having a collapsed delivery configuration and an expanded deployment configuration, the clot engaging device having a proximal end and a distal end and an intermediate body section between the proximal end and the distal end, the clot engaging device being connected to a first elongate shaft element;
   a capture basket located distally of the clot engaging device and having a collapsed delivery configuration and an expanded deployed configuration, the capture basket having a proximal mouth formed by a proximal mouth structure, the proximal mouth being open when the capture basket is in the expanded deployed configuration, a distalmost end of the proximal mouth structure being located at the proximal end of the capture basket, the capture basket being connected to a second elongate shaft element at a first portion of the proximal mouth structure;
   a control tether coupled to the proximal mouth at a second portion of the proximal mouth structure and selectively movable to adjust an orientation of the proximal mouth in the expanded deployed configuration, the second portion of the proximal mouth structure being different than the first portion of the proximal mouth structure, and
   the first and second shaft elements being movable relative to one another such that the clot engaging device is axially movable relative to the capture basket,
   wherein the distal end of the clot engaging device has a radial size smaller than a radial size of the intermediate body section and of the proximal mouth of the capture basket.

2. A clot retrieval apparatus as claimed in claim 1 wherein the clot engaging device is formed of a plurality of struts with at least some of the struts forming closed cells.

3. A clot retrieval apparatus as claimed in claim 1 wherein the clot engaging device includes an open seam forming a pathway for the second shaft element.

4. A clot retrieval apparatus as claimed in claim 1 wherein the proximal mouth structure includes a support frame and the capture basket comprises a capture net coupled to the support frame.

5. A clot retrieval apparatus as claimed in claim 1, wherein each of the first and second shaft elements and control tether extend proximally to the handle.

6. A clot retrieval apparatus as claimed in claim 1, wherein the control tether is movable relative to the first and second shaft elements.

7. A clot retrieval apparatus as claimed in claim 1, wherein the proximal mouth structure includes a frame forming two loops joined at a common point.

8. A clot retrieval apparatus as claimed in claim 7, wherein the two loops are formed by a frame member in a figure-eight pattern.

9. A clot retrieval apparatus as claimed in claim 7, wherein the control tether is connected to one loop, and the second shaft element is connected to the other loop.

10. A clot retrieval apparatus, comprising:
    a handle;
    a clot engaging device located distally of the handle having a collapsed delivery configuration and an expanded deployed configuration, the clot engaging device including a body having
    a plurality of struts forming a plurality of closed cells,
    a proximal end,
    an intermediate section, and
    a distal end, and
    the clot engaging device being connected to a first elongate shaft element; and
    a capture basket located distally of the clot engaging device and having a collapsed delivery configuration and an expanded deployed configuration, the capture basket having a proximal mouth formed by a proximal mouth structure coupled to a control member and open when the capture basket is in the expanded deployed configuration, a distalmost end of the proximal mouth structure being located at the proximal end of the capture basket the control member movable between a first position in which the proximal mouth in the expanded deployed configuration is at a first radial orientation relative to the control member, and a second position in which the proximal mouth in the expanded deployed configuration is at a second radial orientation relative to the control member, the capture basket being connected to a second elongate shaft element at a first location along the proximal mouth structure and the control member being connected to the capture basket at a second location along the proximal mouth structure, the second location being spaced from the first location, and the first and second shaft elements being movable relative to one another such that the clot engaging device is axially movable relative to the capture basket wherein, in the expanded deployed configuration, the distal end of the clot engaging device has a radial size which is smaller than a radial size of the intermediate section and of the proximal mouth of the capture basket.

11. A clot retrieval device as claimed in claim 10 wherein the clot engaging device includes an open seam forming a pathway for the second shaft element.

12. A clot retrieval apparatus as claimed in claim 10 wherein the proximal mouth structure includes a support frame and the capture basket comprises a capture net coupled to the support frame.

13. A clot retrieval apparatus as claimed in claim 10, wherein each of the first and second shaft elements and control member extend proximally to the handle and are movable relative to one another.

14. A clot retrieval apparatus, comprising:
a handle;
a closed-cell cage having a collapsed delivery configuration and an expanded deployment configuration, the closed-cell cage having a proximal end connected to a first elongate member; and
a capture basket located distally of the closed-cell cage and having a collapsed delivery configuration and an expanded deployed configuration, the capture basket having an adjustable mouth structure coupled to a second and third elongate members;
the closed-cell cage having a distal end sized to be received within the adjustable mouth structure of the capture basket,
the first, second, and third elongate members being movable relative to one another, and
a porosity of the closed-cell cage is greater than a porosity of the capture basket.

15. A clot retrieval apparatus as claimed in claim 14, wherein one of the second or third elongate members is a tether connected to a distalmost end of the adjustable mouth structure.

16. A clot retrieval apparatus as claimed in claim 14, wherein the a distalmost end of the adjustable mouth structure is located at a proximal end of the capture basket.

17. A clot retrieval apparatus as claimed in claim 14, wherein the closed-cell cage includes a tubular shape and tapering distal end.

18. A clot retrieval apparatus as claimed in claim 14, wherein at least one of the second or third elongate members extends through an inner portion of the closed-cell cage.

19. A clot retrieval apparatus as claimed in claim 18, wherein the at least one second or third elongate members extending through an inner portion of the closed-cell cage extend through at least one closed cell at the distal end of the closed-cell cage.

20. A clot retrieval apparatus as claimed in claim 18, wherein both the second and third elongate members extending through an inner portion of the closed-cell cage.

* * * * *

UNITED STATES PATENT AND TRADEMARK OFFICE
CERTIFICATE OF CORRECTION

| | | |
|---|---|---|
| PATENT NO. | : 9,463,036 B2 | Page 1 of 1 |
| APPLICATION NO. | : 13/823048 | |
| DATED | : October 11, 2016 | |
| INVENTOR(S) | : Eamon Brady et al. | |

It is certified that error appears in the above-identified patent and that said Letters Patent is hereby corrected as shown below:

In the Claims

Claim 16, Column 10, Line 16, "wherein the a distalmost end" should read --wherein a distalmost end--

Signed and Sealed this
Twenty-seventh Day of December, 2016

Michelle K. Lee
*Director of the United States Patent and Trademark Office*